United States Patent [19]
Iwai et al.

[11] Patent Number: 5,633,083
[45] Date of Patent: May 27, 1997

[54] TOOTHBRUSH

[75] Inventors: Tatsuaki Iwai, Takatsuki; Katsushi Ebisudani, Osaka; Naomi Yokosuka, Daito, all of Japan

[73] Assignees: Sunstar Kabushiki, Takatsuki; Toray Monofilament Co., Ltd., Okazaki, both of Japan

[21] Appl. No.: 276,668

[22] Filed: Jul. 18, 1994

Related U.S. Application Data

[63] Continuation-in-part of Ser. No. 936,725, Aug. 31, 1992, abandoned, which is a continuation of Ser. No. 601,713, Oct. 30, 1990, abandoned.

[30] Foreign Application Priority Data

Mar. 14, 1989 [JP] Japan ..................... 1-62867

[51] Int. Cl.$^6$ ..................... D02G 3/00
[52] U.S. Cl. ............ 428/378; 428/372; 428/375; 428/394; 428/395; 15/167.1; 15/167.2; 424/49
[58] Field of Search ............ 428/378, 394, 428/395, 372; 15/167.1, 162.2, 159.1, 167.3

[56] References Cited

U.S. PATENT DOCUMENTS

| | | | |
|---|---|---|---|
| 2,138,814 | 12/1938 | Bressler | 416/187 |
| 2,670,489 | 3/1954 | Cross et al. | 15/167.1 |
| 2,880,129 | 3/1959 | Billings | 15/167.1 |
| 2,939,164 | 6/1960 | Rosenthal | 15/159.1 |
| 2,965,912 | 12/1960 | Cohen et al. | 15/207.2 |
| 3,076,218 | 2/1963 | Cook et al. | 15/207.2 |
| 3,380,848 | 4/1968 | Horowitz | 427/222 |
| 3,605,163 | 9/1971 | Bechtold | 15/159 |
| 3,956,480 | 5/1976 | Dichter et al. | 424/54 |
| 5,141,290 | 8/1992 | Mairon | 15/167.1 |

FOREIGN PATENT DOCUMENTS

| | | |
|---|---|---|
| 0182523 | 5/1986 | European Pat. Off. . |
| 46-20304 | 6/1971 | Japan . |
| 48-31719 | 9/1973 | Japan . |
| 50-40688 | 11/1975 | Japan . |
| 51-506 | 1/1976 | Japan . |
| 56156074 | 9/1983 | Japan . |
| 2213721 | 8/1989 | United Kingdom . |

OTHER PUBLICATIONS

Derwent Abstracts, Week 8343, 1983, accession No. 83–797950 [43], Derwent Publications, Ltd., London, GB (56–156074 Japan).

*Primary Examiner*—Patrick J. Ryan
*Assistant Examiner*—J. M. Gray
*Attorney, Agent, or Firm*—Foley & Lardner

[57] ABSTRACT

The present invention relates to a toothbrush (a) wherein a filament implant part is non easily contaminated with bacteria even when using for a long period of time. The toothbrush is characterized by implanting of a filament coveted by a coat of a complex of a polymer having cation exchange capacity and a cationic bactericide.

3 Claims, 5 Drawing Sheets

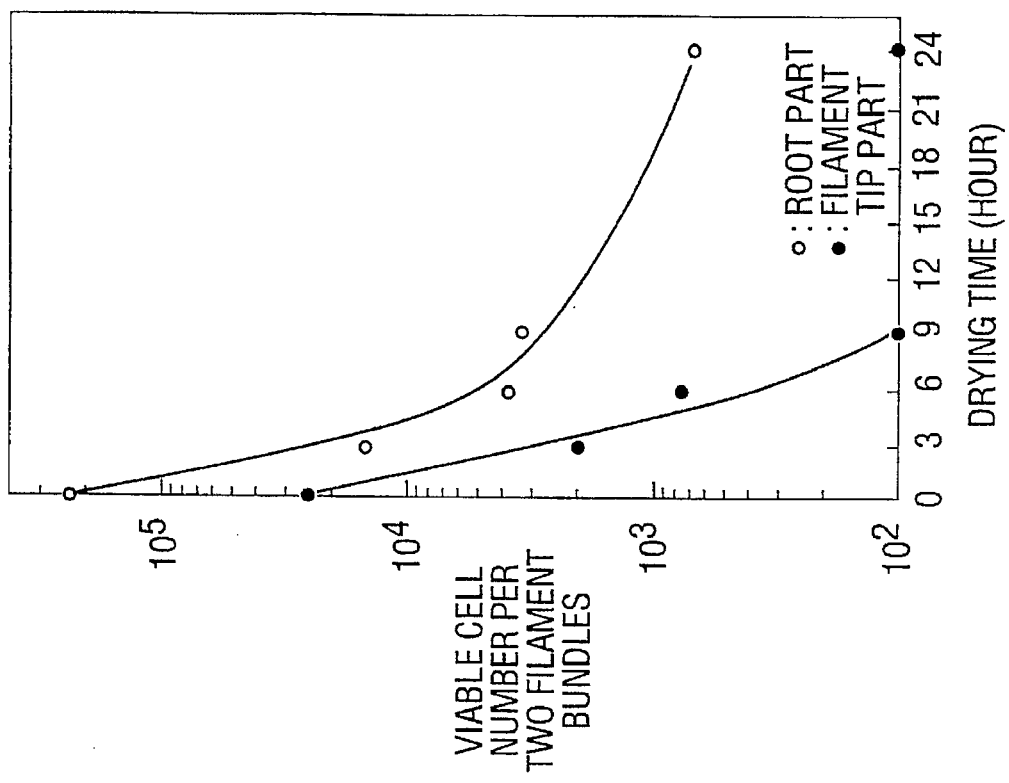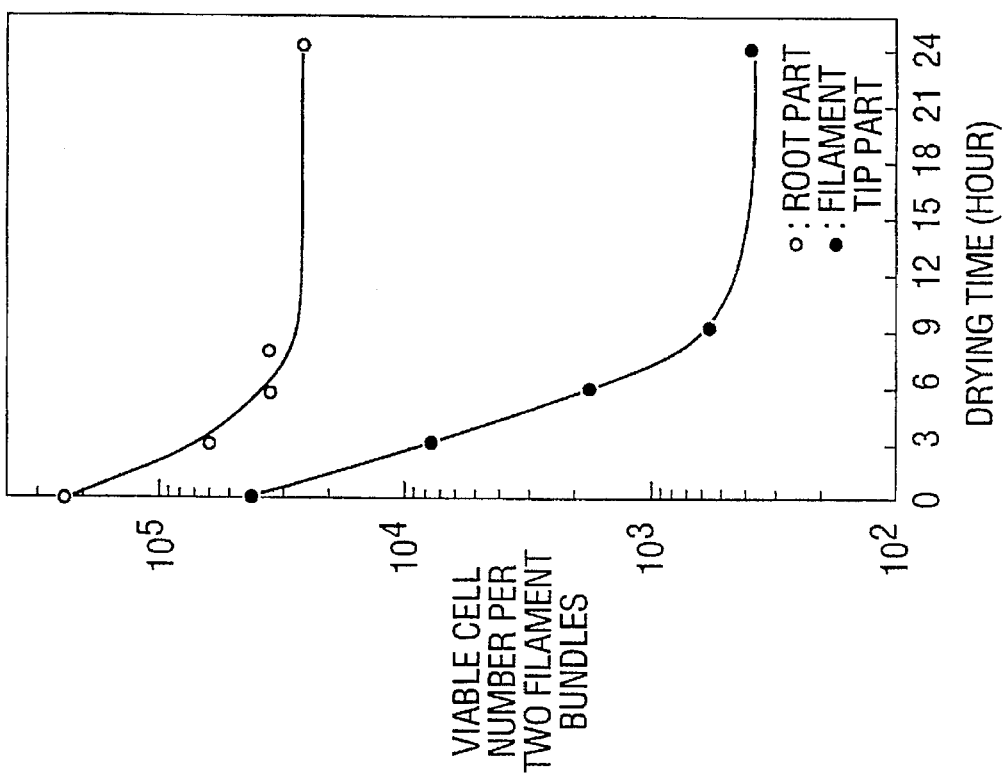

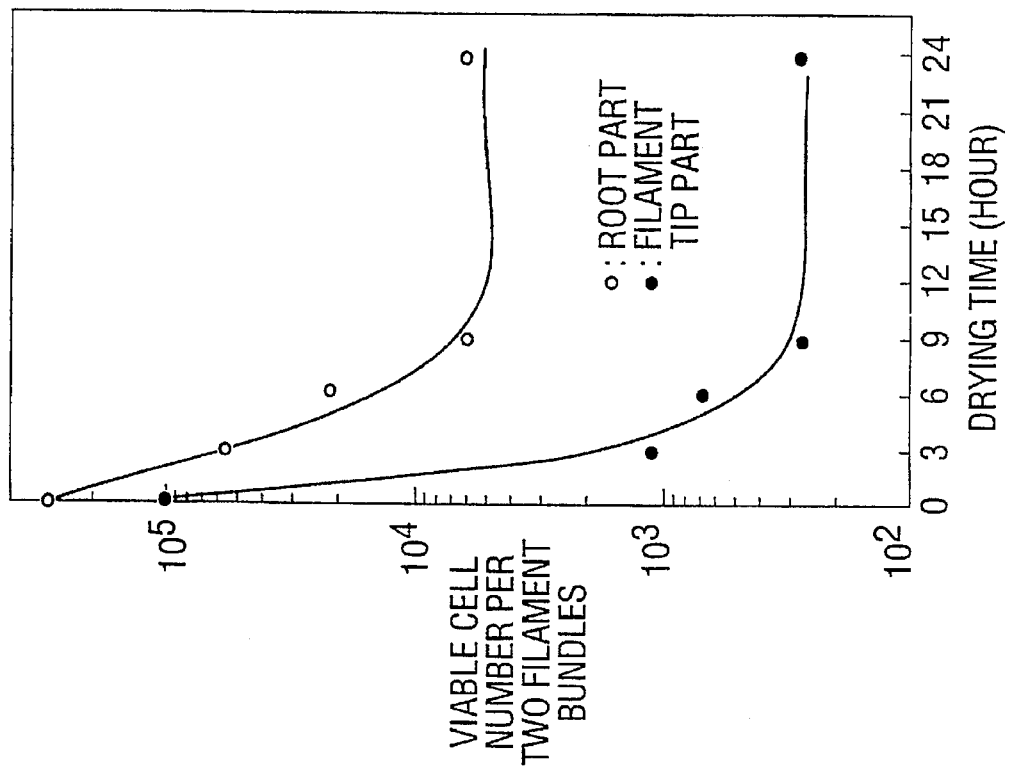
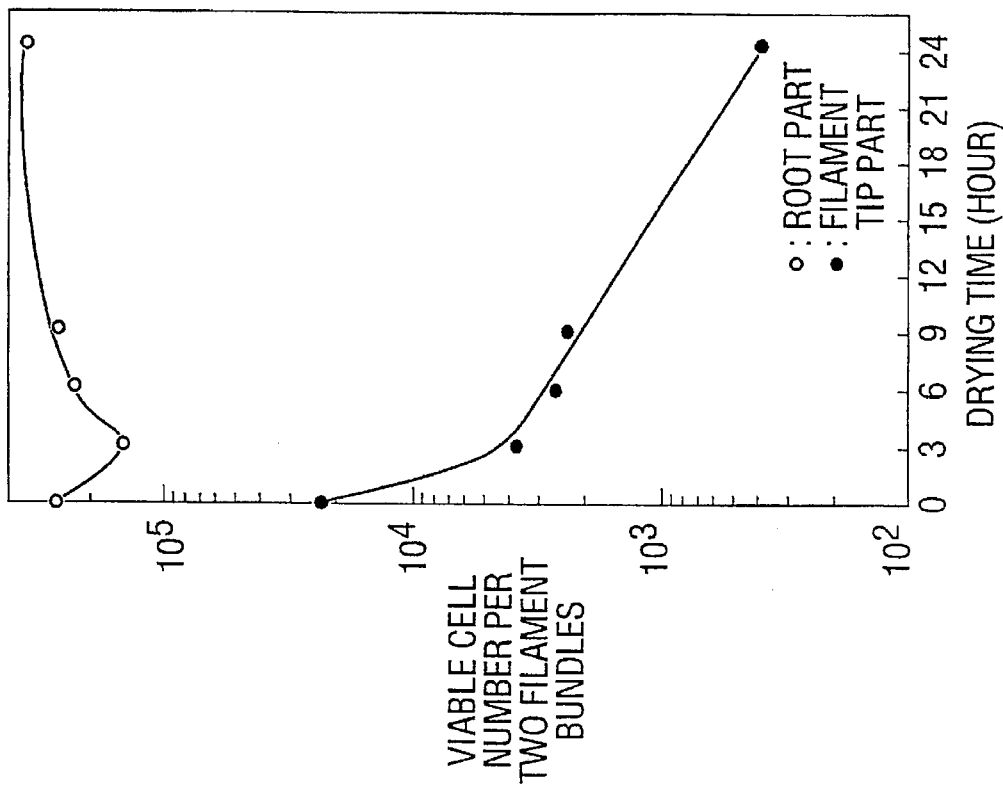

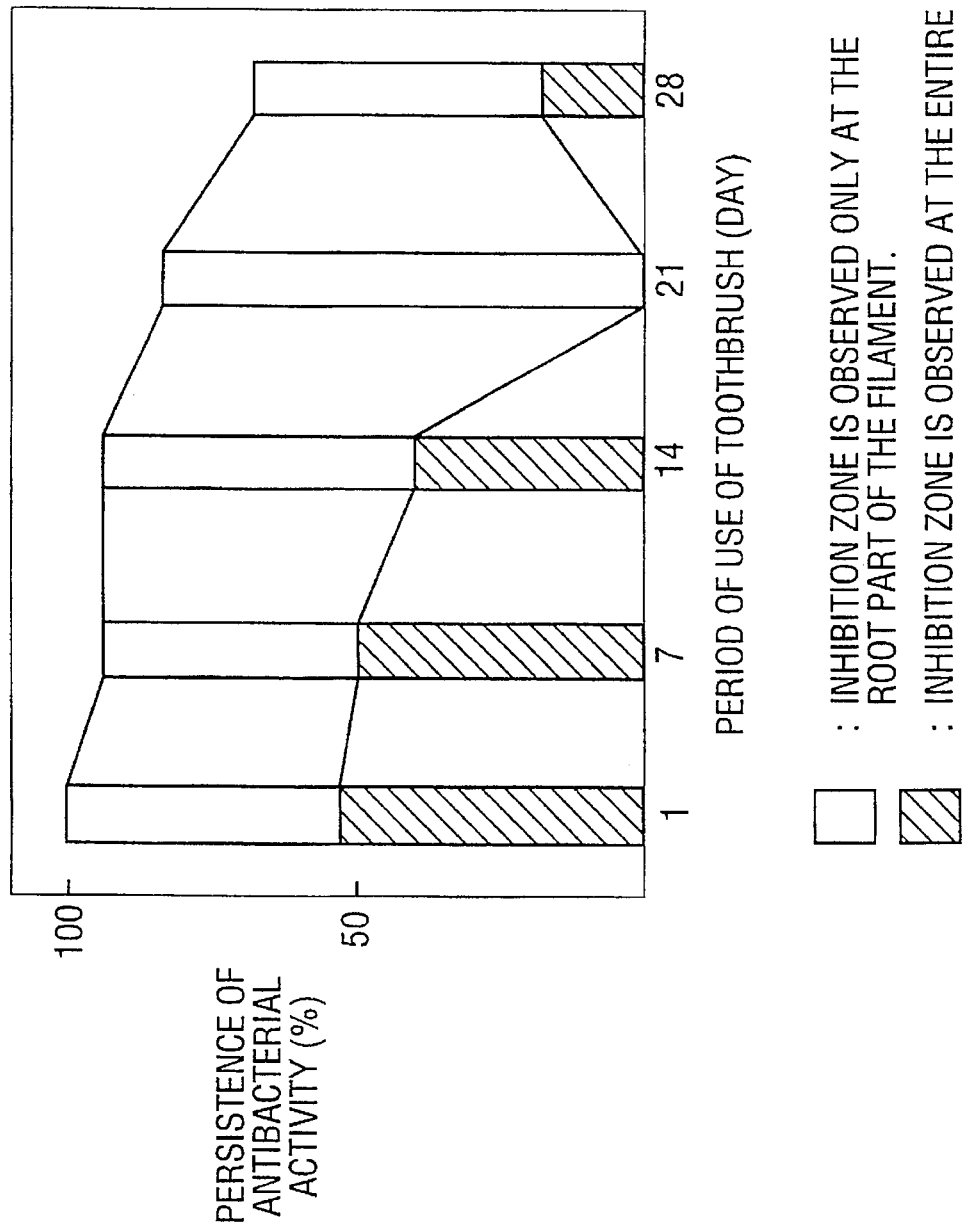

TOOTHBRUSH

CROSS REFERENCE

This is a continuation-in-part application of application Ser. No. 07/936,725 filed Aug. 31, 1992, abandoned which is a continuation application of application Ser. No. 07/601,713 filed Oct. 30, 1990, now abandoned.

FIELD OF THE INVENTION

The present invention relates o a toothbrush he filament implant part of which is hardly contaminated with bacteria even using it for a long period of time.

DESCRIPTION OF THE PRIOR ART

Since a toothbrush is used in the oral cavity, in general, it is produced in a sanitary condition by means of ultraviolet-light irradiation or the like to prevent it from bacterial contamination during its production steps. Then, usually, bacterial contamination is scarcely observed in a toothbrush until is package is unpacked.

However, it has been confirmed hat a toothbrush, particularly, its filament implant pare is contaminated with bacteria in the oral cavity as well as in keeping environment, while brushing of teeth several times per day is continued. Further, it has also been found than the degree of contamination increases as increase in frequency of use [Hiroko Miura et al., "Studies on Bacterial Contamination of Toothbrush", Koku Eisei Kaishi (Journal of dental health) 38, 180–185, 1988 and M. Svanberg, "Contamination of Toothpaste and Toothbrush by *Streptococcus mutans*, Scand. j. Dent. Res., 86, 412–414, 1978].

Hitherto, as a method for controlling bacterial contamination of a toothbrush, it has been said that the desired method is to thoroughly wash a toothbrush with water after use and To keep it at a well-ventilated place. However, this is not readily realized because of housing environment in recent days, and a toothbrush is often kept in insanitary environment. On the other hand, as a more positive method, sometimes, a disinfection treatment such as disinfection by boiling, disinfection by a medicament, for example, alcohol or the like, disinfection by sunning, or the like is employed.

However, these disinfection Treatments take time and, in addition, sometimes, they cause deterioration of physical properties of a materials for the handle or filament of a toothbrush. Therefore, they are rarely employed in practice.

Then, attempts have been made by imparting antibacterial properties to a material for the handle or filament itself to solve the above problem. Particularly, a filament implant part is liable to be contaminated with bacteria because dirt is liable to retain there and such a part is difficult to dry. Therefore, various studies have been made to impart antibacterial properties to a material for the filament and, further, to maintain its activity even using it for a long period time [see Japanese Utility Model Kokoku Nos. 37-21003, 42-19047, 48-31719 and 50-40688 as well as Japanese Patent Kokoku Nos. 46-20304 and 48-27389].

However, the above prior art methods have problems such as high cost due to complicated production steps, deterioration of physical properties of the filament itself, impracticably low antibacterial activity and the like, and most of them are impracticable. Among them, a method comprising applying a polymer solution containing a bactericide on a surface of filament during its production steps (Japanese Patent Kokoku No. 46-20304) has relatively high practicability. However, the bactericide is not in the form suitable for moderate slow release, its antibacterial property is still insufficient.

European Patent No. 182523 discloses an oral hygiene composition comprising a certain polymer having carboxyl group. According to this patent, the polymer is adsorbed on the tooth surfaces to prevent or inhibit adhesion of oral bacteria to the teeth. In addition, the this patent discloses toothbrush bristles coated or impregnated with the composition. However, in view of the disclosure of this patent, the polymer disclosed therein patent must be water-soluble and it dissolves during use and disappears. Therefore, it is insufficient for preventing or inhibiting attachment of bacteria to toothbrush bristles.

Furthermore, U.S. Pat. No. 2,939,164 discloses bactericidal treatment of toothbrush bristles with an organic aromatic mercury compound. However, in view of safety, this compound cannot be used of the oral cavity.

Thus, although various attempts have been done to provide effective antibacterial property to toothbrush, they are still insufficient.

SUMMARY OF THE INVENTION

In order to obtain a toothbrush having excellent antibacterial property which is highly practicable from the viewpoints of productivity, physical properties and cost, the present inventors have studied intensively. As a result, it has been found that the above problem can be solved by coating a surface of a filament with a complex of a polymer having cation exchange capacity and cationic bactericide. Thus, the present invention had been completed.

BRIEF DESCRIPTION OF THE DRAWINGS

FIGS. 2a, 2b, 3a, 3b, 4a and 4b are graphs illustrating bacterial contamination of the toothbrush after using for 1, 8 and 20 days in the antibacterial activity test, respectively.

FIG. 5 is a graph illustrating the result of the durability test of antibacterial activity of the toothbrush of the present invention.

Figure 1A:
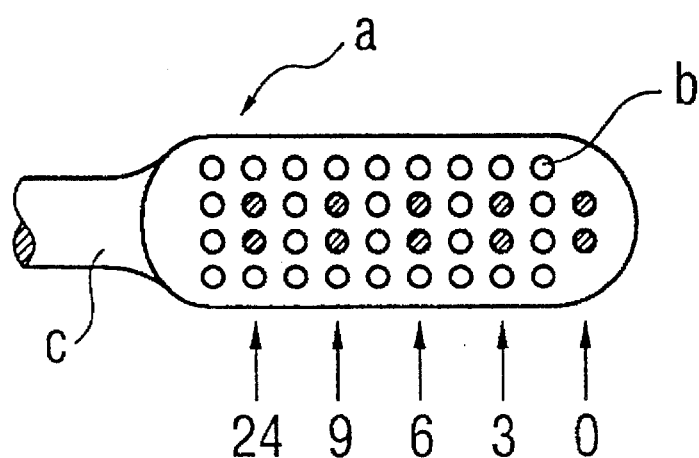
FIG. 1a is a schematic plan view and FIG. 1b is a side view of an implant part of a toothbrush illustrating the sampling and measuring sites of the toothbrush in the antibacterial activity test.

Symbols in the drawings mean as follows.

"a" is a toothbrush, "b" is a filament and "c" is a handle.

DETAILED DESCRIPTION OF THE PREFERRED EMBODIMENTS

According to the present invention, there is provided a toothbrush characterized in that a filament covered by a coat of a complex comprising a polymer having cation exchange capacity and a cationic bactericide is implanted.

The polymer having cation exchange capacity used in the present invention is a polymer produced by polymerizing a monomer suitably substituted with an anionic substituent, for example, carboxyl group, sulfonic group, phenolic hydroxyl group or the like according to the conventional method such as emulsion polymerization, solution polymerization, bulk polymerization or the like. Examples of the monomer include ehylene, propylene, vinyl chloride, vinylidene chloride, vinyl acetate, acrylic esters, acrylonitrile, styrene, acrylamide, methacrylic esters, methacrylamide and the like, and a copolymerizable monomer can be used in combination with thereof. Further, a compound providing a hydrophilic substituent, for example, polyoxyethylene glycol, polyoxypropylene glycol or the like can be added to the polymer used so that water can De used as a solvent for preparing a coating solution or suspension for covering a filament with the complex of the polymer and a cationic bactericide.

As the cationic bactericide, There are benzethonium, benzalkonium, cetylpyridinium, chlorhexidine and the like. Particularly, chlorhexidine is most preferred in view of its broad antibacterial spectrum and high safety.

The complex of the above polymer and bactericide can be prepared by dissolving or suspending these materials in a suitable solvent such as water, an alcohol, for example, methanol, ethanol or the like and, if desired, adding a suitable amount of a cross-linking agent such as a polyfunctional block isocyanate compound to react them. The ratio of the polymer to the bactericide is not specifically limited and varies depending upon the polymer and bactericide to be used. Usually, it is preferable to use 1 to 100 parts by weight of the bactericide per 100 parts by weight of the polymer.

The polymer thus obtained by using a cross-inking agent is water-insoluble. AS shown in Example hereinafter, when the polymer and bactericide together with a cross-lingking agent are dissolved in a suitable solvent and applied to filament no obtain a cross-linked polymer, the polymer becomes water-insoluble and maintains antibacterial activity for a long period of time under normal use conditions.

As the material for filament, known materials such as nylon, polyester, for example, polybutylene terephthalate, polypropylene, polyvinylidene chloride and the like can be used.

Covering of the filament can be carried out by applying a solution or suspension of the polymer and bactericide to the filament according to the conventional method and then drying it.

Implant can also be carried out according to the conventional method.

Thus, in order to produce the toothbrush of the present invention, for example, a material for the filament is melt-extruded according to the conventional method and, after cooling, the extruded material is heat-stretched until its diameter becomes about 100 to 500μ. A predetermined amount of a solution of the complex obtained by dissolving the above polymer and cationic bactericide in a suitable solvent is applied to the surface of the stretched filament material, and it was set and dries in a neat setting furnace to obtain a coating treated filament. Then, this is implanted in a suitable handle to produce the desired toothbrush.

In the present invention, thickness of the coating of the complex for imparting the desired antibacterial properties to the toothbrush is usually 0.1 to 10μ, preferably 0.5 to 5μ.

EXAMPLE

The following Examples further illustrate the present invention in detail.

Example 1

According to the conventional method, a predetermined amount of a mixture obtained by adding a trifunctional blocked isocyanate compound (40 parts by weight, trade name: SUPERFRESH JB-7100) as a cross-linking agent to an aqueous emulsion of a complex of a copolymer (100 parts by weight) of three kinds of monomers, 2-acrylamide-2-methylpropane sulfonic acid, 2-hydroxyethyl acrylate and polyethylene glycol monomethyl ether methacrylate and chlorhexidine (35 parts by weight) was applied on a surface of a heat-stretched filament material (nylon 610) and it was set and dried in a heat setting furnace no produce a filament (diameter: 200μ). Thickness of the coating was to 4μ(average about 2μ).

The resulting filament was implanted according to the conventional method to produce the desired toothbrush.

Antibacterial activity tests of the resulting toothbrush were carried out as follows.

(A) Antibacterial Activity Test (in vitro)

Antibacterial activity was tested by agar plate method according to AATCC test method 90.

The test conditions and test method are as follows.

(i) Test Strain *Staphylococcus aureus* AATCC 6538 was used.

(ii) Preparation of cell suspension

One loopful of the test strain was inoculated in 10 ml of a nutrient medium and was incubated at 37° C. for 18 to 24 hours.

(iii) Composition of Agar Medium pH was adjusted to 7.0 to 7.2.

| | |
|---|---|
| Peptone | 10 g |
| Beef extract | 5 g |
| Sodium chloride | 5 g |
| Distilled water | 1000 ml |
| Agar | 15 g |

(iv) Test Method

The agar medium having the above composition was prepared, sterilized in an autoclave, and placed in an incubator maintained at 45° C. After the temperature became constant, 1 ml of the above-prepared cell suspension was added to 150 ml of the medium. 15 ml portions of the inoculated agar medium were distributed into sterilized petri dishes and allowed to stand for 15 minutes. The filament sample cut to about 30 mm was gently placed on the surface of the agar medium, fixed and then incubated at 37° C. for 18 to 24 hours. As a control, the same test was carried out by using a filament having the same diameter without covering the complex coating.

As a result, an inhibition zone was clearly observed around the complex coated filament of the present invention, while no inhibition zone was observed in the control filament.

(B) Antibacterial property test (in vivo)

The test conditions and test method are as follows.

(i) Subjects

The subjects were 10 volunteers aged 19 to 40 without serious systematic and oral diseases.

(ii) Toothbrush to be tested

A toothbrush handle having 38 holes of 4 lines×10 rows and 1.7 mm in hole diameter was implanted with the filaments of the present invention covered with the complex coating (hereinafter referred to as the antibacterial-treated filaments), or control filaments having the same diameter without covering the complex coating (hereinafter referred to as non-treated filaments) according to the conventional method, and then the filaments were cut to 10.5 mm in length to produce a toothbrush to be tested.

(iii) Test Method

The subjects were requested to brush their teeth twice a day for each three minutes, freely. Since there was a possibility than a test result was influenced by an ingredient of a toothpaste, the subjects were prohibited from using any toothpaste. After completion of brushing, the implant part of the toothbrush was washed with running water for 10 seconds. In order to prevent bacterial contamination by the fingers, the subjects were prohibited from touching the implant part by the fingers. After use, the toothbrush was dried and kept in a thermo-hygrostat maintained at a temperature of 20° C. and a relative humidity of 65% in a state that the toothbrush was set up with holding the implant part upper until the next use. The nest was repeatedly conducted under the above conditions with respect to the toothbrush implanted with antibacterial-treated filaments of the present invention and the non-treated toothbrush, respectively. The three test periods of 1, 8 and 20 days were employed.

(iv) Sampling of Filament Bundle

Figure 1B:
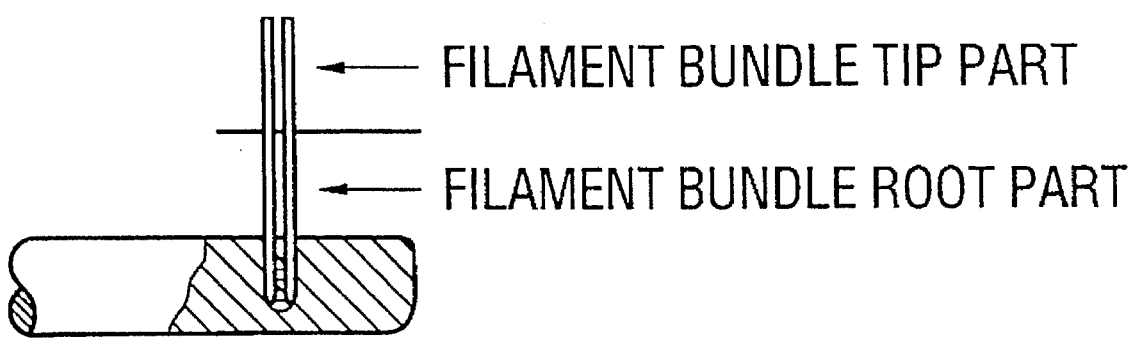

Since the number of contaminative bacteria varies depending upon a drying time, two bundles of filaments of the test toothbrush were sampled with the elapse of drying time as shown in FIG. 1 and the number of contaminative bacteria was counted. The numbers 0, 3, 6, 9, and 24 directly below FIG. 1 are the elapsed drying time for each corresponding sample of bundles. The filament bundle sampled was cut into two parts, i.e., filament tip part and root part and the numbers of bacteria of bosh parts were counted, respectively.

(v) Count of Bacteria

The filament bundle sampled as described above was placed into a test tube and 10 ml of PBS was added thereto and strongly agitated. The resulting bacteria suspension was stepwisely diluted and 0.1 ml of a dilution was smeared on a blood agar medium according to the conventional method. After it was incubated at 35° C. for 48 hours, the viable cell number was counted.

The results are shown in FIG. 2 to FIG. 4.

FIG. 2a represents the bacterial contamination after use for 1 day for a non-treated filament, whereas FIG. 2b represents the bacterial contamination after use for 1 day for an antibacterial treated filament.

FIG. 3a represents the bacterial contamination after use for 8 days for a non-treated filament, whereas FIG. 3b represents the bacterial contamination after use for 8 days for an antibacterial treated filament.

Figure 4B:
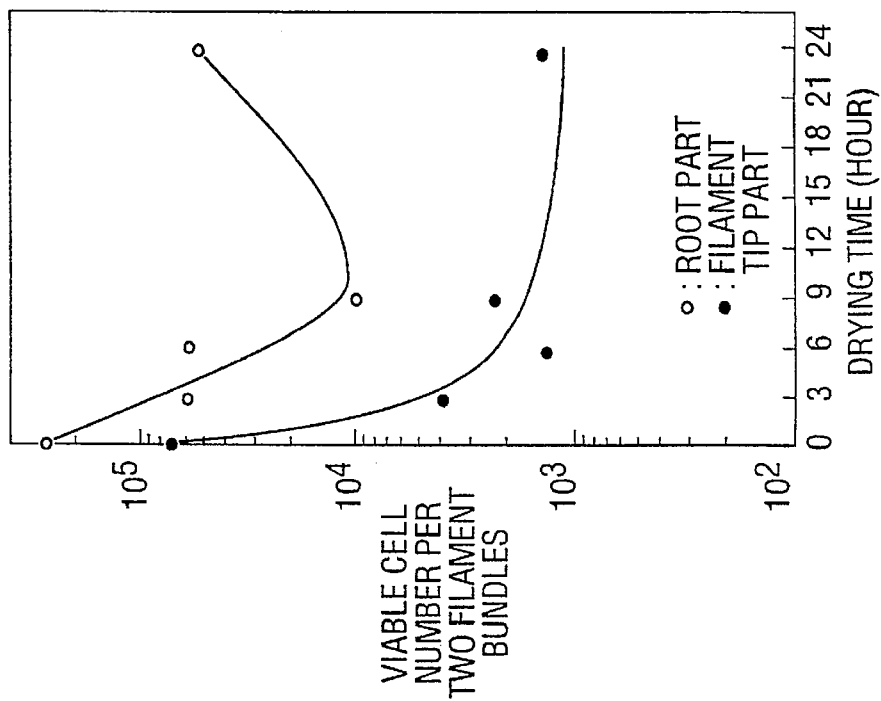
Figure 4A:
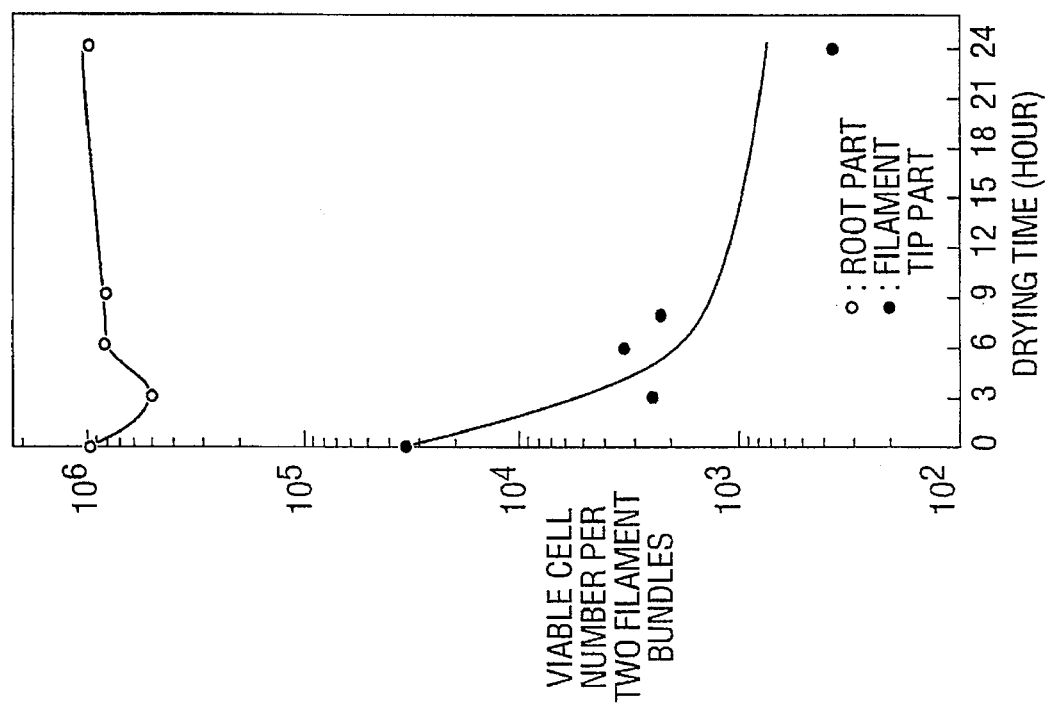

FIG. 4a represents the bacterial contamination after use for 20 days for a non-treated filament, whereas FIG. 4b represents the bacterial contamination after use for 20 days for an antibacterial treated filament.

As is clear from FIG. 2 to FIG. 4, the degree of bacterial contamination of the antibacterial-treated filaments is lower than that of the non-treated filament and, in both filaments, the degree of bacterial contamination of the root part is higher than that of the tip part. Further, it has been found that the antibacterial-treated filaments show higher antibacterial activity at the root part where the higher degree of antibacterial contamination is observed.

(C) Lasting of Antibacterial Activity

The test conditions and test method are as follows.

(i) Subjects

The subjects were 5 volunteers aged 27 to 35 without serious systematic disease or oral disease.

(ii) Toothbrush to be Tested

The toothbrush handle having 38 holes of 4 lines×10 rows and 1.7 mm in hole diameter was implanted with the antibacterial-treated filaments of the present invention according to the conventional method and the filaments were cut to 10.5 mm in length to produce a toothbrush no be tested.

(iii) Test Method

The subjects were requested to brush their teeth three times a day, freely. Further, they were not prohibited from using a toothpaste. A method for keeping the toothbrush was not limited.

(iv) Sampling of Filaments

On 1, 7, 14, 21 and 28 days after starting the test, three filaments were drawn at random per one toothbrush as the test sample.

(v) Evaluation of Antibacterial Activity

Evaluation was conducted out by agar plate method according to the above AATCC test method 90.

The results are shown in FIG. 5.

As is clear from FIG. 5, it has been found that the antibacterial-treated filaments of the present invention maintain antibacterial activity at the root part where bacterial contamination is particularly high even after using it for 28 days and the filament has sufficient durability in practice.

(D) Physical Property Test of Filament (Hardness test)

The test conditions and test method are as follows.

(i) Toothbrush to be tested

The same toothbrush as that used in the antibacterial activity test (in vivo) was used. (Thirty toothbrushes were used, respectively.)

(ii) Test Conditions

In a thermo-hygrostat maintained at a temperature of 20° C.±1° C. and a relative humidity of 65±5%, a buckling hardness was measured by perpendicularly compressing the filament tip surface of the implant part of the toothbrush. Autograph DSS-2000 manufactured by Shimadzu SeisaKusho was used as the measuring equipment.

The results are shown in Table 1.

As is clear from Table 1, it has been found that there is no difference in physical properties between the antibacterial-treated filament of the present invention and that of the non-treated filament.

TABLE 1

|  | Toothbrush implanted with antibacterial-treated filament | Toothbrush implanted with non-treated filament |
| --- | --- | --- |
| Average value (kg) | 7.11 | 7.08 |
| Standard deviation (kg) | 0.45 | 0.48 |

Effect of the Invention

As described above, according to the present invention, the antibacterial-treated filaments are used and, therefore, a toothbrush wherein filaments having such an excellent antibacterial activity that the activity can be maintained even for more than one month of use as well as having the same physical property as that of the conventional filaments are implanted can be mass-produced at low cost.

What is claimed is:

1. A toothbrush comprising:

a plurality of filaments;

a bactericidal coating on said filaments for inhibiting bacterial growth, wherein said bactericidal coating includes a complex of bactericide with a polymer capable of cation exchange and a cross-linking agent, wherein said bactericide is selected from the group consisting of chlorhexidine, cetylpyridinium, benzalkonium and benzethonium, wherein said polymer is selected from the group consisting of vinyl chloride, vinylidene chloride, vinyl acetate, acrylic ester, acrylonitrile, styrene, ethylene, propylene, acrylamide, methacrylic ester, methacrylamide and a copolymer thereof, wherein said polymer has an anionic substituent selected from sulfonic group;

wherein said bactericidal coating is from 0.1 to 10 μm thick; and wherein said plurality of filaments are made of a material selected from the group consisting of nylon, polyester, propylene and polyvinylidene chloride.

2. A toothbrush according to claim 1, wherein said cross-linking agent is a polyfunctional blocked isocyanate compound.

3. A toothbrush according to claim 1, wherein the bactericide is used in an amount of 1 to 100 parts by weight per 100 parts by weight of said polymer.

* * * * *